United States Patent
Brunner et al.

(10) Patent No.: US 7,742,557 B2
(45) Date of Patent: Jun. 22, 2010

(54) METHOD FOR GENERATING A 3D RECONSTRUCTION OF A BODY

(75) Inventors: Thomas Brunner, Nürnberg (DE); Benno Heigl, Coburg (DE); Holger Kunze, Bubenreuth (DE); Florian Vogt, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 201 days.

(21) Appl. No.: 12/156,932

(22) Filed: Jun. 5, 2008

(65) Prior Publication Data
US 2008/0304617 A1 Dec. 11, 2008

(30) Foreign Application Priority Data
Jun. 5, 2007 (DE) .................. 10 2007 026 115

(51) Int. Cl.
*A61B 6/00* (2006.01)
(52) U.S. Cl. .......................................... 378/4
(58) Field of Classification Search ............... 378/4, 378/207
See application file for complete search history.

(56) References Cited

U.S. PATENT DOCUMENTS

| | | | |
|---|---|---|---|
| 5,319,693 A | | 6/1994 | Eberhard et al. |
| 5,740,224 A | * | 4/1998 | Muller et al. ............... 378/11 |
| 6,944,260 B2 | * | 9/2005 | Hsieh et al. ............... 378/19 |
| 2004/0179643 A1 | | 9/2004 | Gregerson et al. |
| 2008/0089468 A1 | * | 4/2008 | Heigl et al. ............... 378/20 |
| 2008/0226021 A1 | * | 9/2008 | Holt ............... 378/14 |

FOREIGN PATENT DOCUMENTS

DE 10 2006 041 033 3/2008

OTHER PUBLICATIONS

Fieldkamp et al., "Practical Cone-beam Algorithm", JOSA A1, 612 (1984), J. Opt. Soc. Amer. A, vol. 1, No. 6, Jun. 1984, pp. 612-619, Journal of the Optical Society of America, Magazine, 1984.
Katsevice, "Image Reconstruction for the Circle-and-Arc Trajectory", Phys Med Biol., May 21, 2005, 50(10), pp. 2249-2265, Epub Apr. 27, 2005., Magazine; 2005.

(Continued)

*Primary Examiner*—Edward J Glick
*Assistant Examiner*—Alexander H Taningco

(57) ABSTRACT

The invention relates to a method for generating a 3D reconstruction of an especially large body that cannot be captured by a single projection by capturing at least two projections, which together capture the body, at each of the positions taken up by a C-arm X-ray unit. Data from the two projections is projected onto a virtual detector and the data from the virtual detector is then used for the filtered back projection procedure. It is assumed here that the real source remains motionless and that only the detector moves. A virtual detector D1'/D2' is only used in order to carry out large scale filtering in the event that real sources Q1 and Q2 for the two projections do not coincide. A return is then made to two independent projections. These two independent projections are used separately in the filtered back projection procedure to generate the 3D reconstruction.

14 Claims, 1 Drawing Sheet

OTHER PUBLICATIONS

Pack et al., "Cone-beam reconstruction using 1D filtering along the projection of M-lines". inverse Problems 21 1105-1120, Print publication: Issue 3, Published Apr. 29, 2005, Book, 2005.

Katsevich, "Image reconstruction for the circle and line trajectory", Phys. Med. Biol. 49 5059-5072 Print publication: Issue 22, Nov. 21, 2004, Received Apr. 26, 2004, in final form Sep. 16, 2004, Published Oct. 25, 2004, pp. 5059-5072, Others, 2004.

Xuan Liu et al.,"Cone-beam Reconstruction for a C-arm CT system", IEEE Nuclear Science Symposium Conference Record 2001, pp. 1489-1493, vol. 3, Others.

Riddell et al., "Rectification for Come-Beam Projection and Backprojection", IEEE Transactions on Medical Imaging 2006, pp. 950-962, vol. 25, Others.

* cited by examiner

METHOD FOR GENERATING A 3D RECONSTRUCTION OF A BODY

CROSS REFERENCE TO RELATED APPLICATIONS

This application claims priority of German application No. 10 2007 026 115.4 filed Jun. 5, 2007, which is incorporated by reference herein in its entirety.

FIELD OF THE INVENTION

The invention relates to a method for generating a 3D reconstruction of a body.

BACKGROUND OF THE INVENTION

A 3D reconstruction is a data set in which individual volume elements (voxels) of a body are assigned numerical values (gray scale values). The compound view provides information about the structure of the body. 3D reconstructions are usually generated by capturing a sequence of two-dimensional images (projections) from different angles. The different angles are created by rotating—that is to say progressively changing the position of—a C-arm X-ray unit on which are mounted an X-ray source and an X-ray detector. Each projection (i.e. each image captured) is then back-projected in three dimensions. It is usually assumed in this method that the X-ray beam attenuates at an even rate along a projection beam from the X-ray source to the X-ray detector. Structures are apparent in the 3D reconstruction due to the large number of projections involved in the method.

One problem with the 3D reconstruction when working with larger bodies is that due to its limited size, the X-ray detector only captures a fan beam that does not fully cover the body under investigation. There are, in other words, some regions of the body that do not appear in the image at the X-ray detector.

DE 10 2006 041 033.5, which was published subsequent to the filing date of the present application, describes a solution to the problem of wide bodies in which two (or even more than two) projections are captured at each of the positions taken up by the C-arm X-ray unit and in which the focus detector system is rotated between projections. It is assumed here that the X-ray source remains in the same position.

The two projections are mapped onto a virtual detector by means of what is known as homography so as to produce a larger combined image that captures the entire object. This combined image is then reconstructed using a conventional reconstruction method (for example making use of what is known as the Feldkamp algorithm). A filter that extends across horizontal rows in the detector is usually employed. This filter may be a ramp filter or a Hilbert filter.

A necessary condition implicit in the generation of the virtual detector in the method filed previously is that the X-ray source does not move in a translational manner between the two projections. However effects associated with the control technology, the structure of the C-arm X-ray unit and the mobility of the latter can lead to a situation in which the source position for the two projections is no longer the same and in which the two projections actually have different source positions. This means that the projections can no longer be superimposed without the appearance of artifacts. The artifacts appear in the 3D reconstruction of the body when it is generated.

SUMMARY OF THE INVENTION

The object of the invention is to disclose a way of preventing artifacts of the type mentioned when using the method from DE 10 2006 041 033.5.

This object is achieved by a method as claimed in the claims.

The method according to the invention accordingly entails the following steps:

a) capture of pairs of X-ray projections from each of a large number of positions assumed by a C-arm X-ray unit on which are mounted an X-ray source and an X-ray detector, wherein, with the X-ray source being held in the same position as far as possible, the first projection of the pair of projections is captured from a first relative positioning of X-ray source and X-ray detector and the second projection of the pair of projections is captured from a second relative positioning of X-ray source and X-ray detector, b) completion of the following steps for each pair of projections:

b1) mapping of the projection data from the first projection onto a virtual detector and mapping of the projection data from the second projection onto the same virtual detector, b2) filtering in such a way as to generate mapping data that originates from both the projection data from the first projection and the projection data from the second projection, b3) reversal of the mapping of the projection data to generate a first projection modified by the filtering and a second projection modified by the filtering, b4) use of both modified projections independently of each other in a filtered back projection procedure to generate the 3D reconstruction.

In contrast to DE 10 2006 041 033.5, in which the data projected onto the virtual detector is back-projected, that is to say in which both projections are added inseparably together to the 3D reconstruction, the projections in the present instance are used separately in the filtered back projection procedure. It is not the case, however, that these projections are used separately from each other in just the form in which they were captured. The filtering is intended to be long trajectory filtering and to cover the entire width of the body to be imaged, so the projections are combined on the virtual detector. This makes it possible to apply long trajectory filtering, for example a ramp filter or Hilbert filter technique, so that the properties of at least a portion of the data (gray scale values of individual pixels of the digital X-ray projection) are such that it could not have originated from just one of the two projections but rather includes data from both projections. It is, however, intended to use the two projections separately from each other in the filtered back projection procedure, so a further separation step is completed after filtering.

It is possible to define a single virtual detector onto which the two projections are mapped by means of homography. The homography can then be reversed after filtering to obtain the modified projections.

It has proven to be expedient to use a separate virtual detector to carry out the filtering for each of the two projections in the pair of projections. The virtual detector may thus be equivalent to the real detector for one of the two projections, for example the first projection, in which case the aforementioned mapping of the projection data (gray scale values of the pixels in the projection) from the first projection is nothing other than a one-to-one mapping. The projection data from the second projection is then mapped by calculating a linking beam between the real source determined (possibly by means of capturing calibration images), as specified for the first projection, and the real detector, as specified for the second projection. Projection data (that is to say gray scale values) assigned to the real detector (that is to say to its pixels) in the second projection is then placed at the point of intersection of the linking beam and the virtual detector. The terms real detector and real source denote a geometric construct that accurately describes the relative geometric positioning of the source and detector as it was during the projections so that the beam path can be reproduced.

The virtual detector is thus nothing other than an extended detector. Data from the second projection appears only at the edge of the projection data on the original detector. All that then has to be done after filtering is to omit the additional portion. What this means is that those data locations on the virtual detector (that is to say pixels) that were points of intersection of the linking beam of the link between the real source in the first projection and the real detector in the second projection are subsequently omitted again.

Naturally this step produces a first projection that has been filtered using data from the second projection. The opposite—a second projection that has been filtered using data from the first projection—can be produced by repeating steps b1) to b3) with the mapping defined as above but with the roles of first and second projection reversed. What this means in other words is that the virtual detector is then equivalent to the real detector in the second projection, for which the one-to-one mapping is used. The real source in the second projection is linked to the detector in the first projection and the data from the first projection is added at the points of intersection of the linking beam with the virtual detector, which is the enlarged real detector in the second projection. The filtering procedure is then applied to produce the filtered second projection, in which the data locations (pixels) that were defined as points of intersection are omitted.

If a suitable filtering method is chosen, there will be a specific correlation between the data from the first projection and the data from the second projection. Consequently it is not absolutely essential for the purposes of the filtered back projection procedure to treat the two projections as though they were projections from different positions of the C-arm X-ray unit. The fact that the projections are assigned to the same position of the C-arm X-ray unit can be accounted for by applying certain weightings. The projection data from both projections can be weighted for the filtered back projection procedure using a weighting function defined on the basis of the pixel data of one virtual detector. This is once again somewhat similar to the virtual detector disclosed in DE 10 2006 041 033.5.

The weighting function does not necessarily ensure that data originating from individual volume elements is equally weighted, so a voxel-by-voxel normalization may be carried out for the 3D reconstruction following step b4).

BRIEF DESCRIPTION OF THE DRAWINGS

A preferred embodiment of the invention is described below with reference to the drawing, in which.

DETAILED DESCRIPTION OF THE INVENTION

Figure 1:
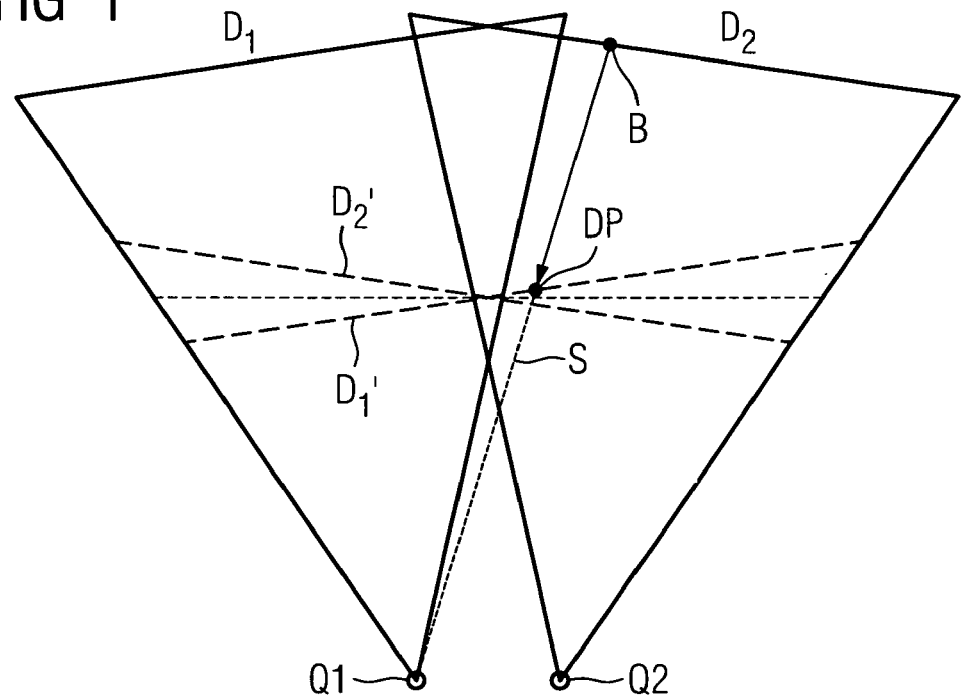
FIG. 1 shows the arrangement of the real X-ray source and X-ray detector in the method according to the invention in schematic form and FIG. 2 shows a virtual detector and a weighting function for the arrangement of FIG. 1.
Figure 2:
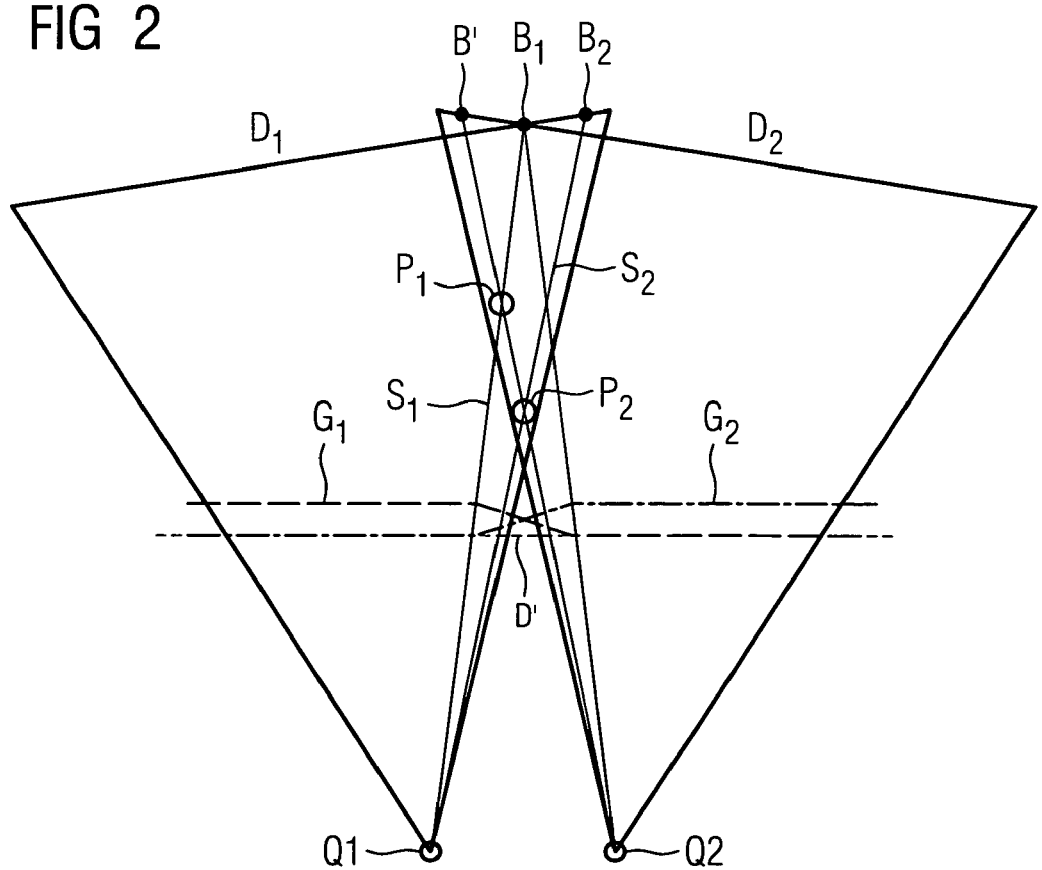

A 3D reconstruction of a body is generated by capturing a sequence of digital X-ray images. Two such digital X-ray projections are generated with a C-arm X-ray unit in a predefined position. The elements of the assembly comprising X-ray source and X-ray detector on the C-arm are rotated relative to each other, with the C-arm X-ray unit in a predefined position, between the capture of the first projection of the pair of projections and the second projection of the pair of projections. It is envisaged that the X-ray source remains in the same position. In practice the X-ray source tends to change position at least slightly. In FIG. 1 the position of the X-ray source for the first image is labeled Q1 and the position of the X-ray source for the second image is labeled Q2. The course of the X-ray detector for the first projection is labeled D1 and the course of the X-ray detector for the second projection is labeled D2. The geometric course of the X-ray detector may be designated the "real detector for the projection". DE 10 2006 041 033.5 discloses that a virtual detector can be generated from the real detector and that this virtual detector captures the data for both projections. However this document assumes that Q1 equals Q2, which is not always the case in reality. If Q1 does not equal Q2, as shown in FIG. 1, the method presented in DE 10 2006 041 033.5 must be adapted somewhat:

Two virtual detectors D1' and D2' are defined. These two virtual detectors are in this case nothing other than extensions of the real detectors D1 and D2. FIG. 1 shows the detectors displaced in parallel for the sake of simplicity. Firstly, all of the gray scale values from the projection that was obtained with the real detector D1 are assigned to the virtual detector D1'. However the virtual detector D1' extends over a somewhat larger area so that a larger body that cannot be imaged in a single projection alone can be captured to produce a full set of data. Data from the second projection now has to be mapped onto the virtual detector D1'. To this end a large number of beams are defined that link pixels on the real detector D2 with the source Q1. Beam S is indicated by way of example. Beam S links a pixel B on the real detector D2 with the real source Q1. Pixel B is assigned a certain gray scale value. Next, this gray scale value is transferred from the real detector D2 to the virtual detector D1': data point DP contains the same gray scale value as point B. Data is assigned to the virtual detector D2' in an analogous process so that the data assigned to the larger part of the virtual detector D2' is the data from the real detector D2 and the data assigned to the left-hand area of D2' in FIG. 1 is data from D1, which is transferred by ascertaining projection beams from the real source Q2 to the real detector D1. Once again the data for certain pixels is assigned to the point of intersection of the linking line in the same way that the data for pixel B is assigned to the point of intersection DP.

Once gray scale values have been assigned to the individual data points (pixels) for the virtual detector D1', large-scale filtering of the data can be carried out. It is possible to use what is known as a ramp filter, which processes individual horizontal detector rows as a whole. This means that data that originates from the real detector D1 (that is to say the first projection) is processed together and simultaneously with data that originates from the real detector D2 (that is to say from the second projection) in a single filtering step. The effect of this is that data points in the left-hand area of the virtual detector D1' in FIG. 1 are assigned gray scale values that are influenced by the gray scale values from the right-hand area and vice versa. The next step in the process is to omit the gray scale values from the virtual detector D1' constructed with reference to beam S and similar beams and then to do the same by analogy for D2'. The virtual detector D1' is truncated in such a way that once again nothing remains but the real detector D1, and the virtual detector D2' is truncated in such a way that once again nothing remains but the real detector D2. No detector D1 and D2 is sufficient on its own to image a specific body to be imaged across its entire width. The method has created a situation in which, starting with a first and second projection, an image is mapped onto a virtual detector D1' and D2', a filtering step is then carried out and the data is finally separated again such that eventually the first projection is recovered again in a modified form, that is to say filtered, and the second projection is similarly recovered again in a modified form, that is to say also filtered.

The two projections can now be used in a filtered back projection procedure to generate a 3D reconstruction.

The aim of the back projection is to image in its entirety a broad body that cannot be imaged in its entirety by the individual real detectors D1 and D2. The data used in the edge areas is data exclusively from the detector D1 or exclusively from the detector D2. However the detectors D1 and D2 have an area of overlap. Both projections can be used simultaneously for this area of overlap. If the real sources Q1 and Q2 happen to coincide, each of the two projections can simply be multiplied with a constant weighting function prior to the back projection procedure. The weighting function can be defined as a crossfade function on a virtual detector. The sources Q1 and Q2 in the current case do not coincide. The effect of this is that an X-ray beam emitted by source Q2 that strikes the real detector D2 passes through both point P1 and point P2. A weight defined for the pixel B' on the detector D2 thus simultaneously applies to volume elements around the point P1 and volume elements around the point P2. However from the point of view of X-ray source Q1, the points P1 and P2 do not lie on the same beam: the beam S1, which passes through the point P1, strikes a different pixel B1 of the real detector D1 to the beam S2, which passes through the point P2 and actually strikes pixel B2. Consequently the volume elements around the point P1 would receive different weights in a weighting procedure to the volume elements around the point P2.

In the present case a suitable weighting for the area of overlap is generated by mapping the projections (homography) onto a virtual detector D1' and D2'. A weighting function G1, which is assigned to the pixels of the real detector D1, and a weighting function G2, which is assigned to the pixels of the real detector D2, are used for the virtual detector D1' and D2'.

The non-coincidence of the sources Q1 and Q2 may cause the sum of the weights in the back projection procedure to have a value other than one. A voxel-by-voxel normalization of the image is then carried out in which the location-dependent weights are used.

The present invention avoids artifacts attributable to the non-coincidence of the real sources Q1 and Q2 by using the two projections independently of each other in the filtered back projection procedure. However the gray scale values of the projections are subjected to a filtering step in which the other projection in each case is considered, with the consequence that long trajectory effects in a body that is to be imaged but could not be imaged in its entirety using just a single projection are accounted for.

The invention claimed is:

1. A method for generating a 3D reconstruction image of a patient, comprising:

providing a C-arm X-ray unit on which mounted an X-ray source and an X-ray detector;
capturing a first projection of the patient by the C-arm X-ray unit from a first relative positioning of the X-ray source and the X-ray detector;
capturing a second projection of the patient by the C-arm X-ray unit from a second relative positioning of the X-ray source and the X-ray detector;
mapping a first projection data of the first projection onto a virtual detector;
mapping a second projection data of the second projection onto the virtual detector;
filtering the first mapping data in such a way as to generate mapping data that originates from both the first projection data and the second projection data;
filtering the second projection data in such a way as to generate mapping data that originates from both the first projection data and the second projection data;
generating a modified first projection by a reversal of the filtered first mapping data;
generating a modified second projection by a reversal of the filtered second mapping data; and
generating the 3D reconstruction image using a filtered back projection procedure based on the modified first projection and the modified second projection independently.

2. The method as claimed in claim 1, wherein the virtual detector is equivalent to the X-ray detector in the first projection.

3. The method as claimed in claim 2, wherein the mapping of the first projection data of the first projection is a one-to-one mapping.

4. The method as claimed in claim 3, wherein the mapping of the second projection data of the second projection is carried out by calculating linking beams between the X-ray source in the first projection and pixels on the X-ray detector in the second projection.

5. The method as claimed in claim 4, further comprising placing the second projection data assigned to the pixels on the X-ray detector in the second projection at intersection points of the linking beams and the virtual detector.

6. The method as claimed in claim 5, wherein the reversal of the filtered first and the reversal of the filtered second mapping data omit data from the second projection that are at the intersection points.

7. The method as claimed in claim 1, wherein the virtual detector is equivalent to the X-ray detector in the second projection.

8. The method as claimed in claim 7, wherein the mapping of the second projection data of the second projection is a one-to-one mapping.

9. The method as claimed in claim 8, wherein the mapping of the first projection data of the first projection is carried out by calculating linking beams between the X-ray source in the second projection and pixels on the X-ray detector in the first projection.

10. The method as claimed in claim 9, further comprising placing the first projection data assigned to the pixels on the X-ray detector in the first projection at intersection points of the linking beams and the virtual detector.

11. The method as claimed in claim 10, wherein the reversal of the filtered first mapping data and the reversal of the filtered second mapping data omit data from the first projection that are on the intersection points.

12. The method as claimed in claim 1, wherein the first and the second projection data are weighted for the filtered back projection procedure using weighting functions.

13. The method as claimed in claim 12, wherein the filtered back projection procedure is followed by a voxel-by-voxel normalization for generating the 3D reconstruction image.

14. An X-ray image device for examining a patient, comprising:

a C-arm X-ray unit on which mounted an X-ray source, and an X-ray detector that:

captures a first projection of the patient from a first relative positioning of the X-ray source and the X-ray detector, and captures a second projection of the patient from a second relative positioning of the X-ray source and the X-ray detector; and a computer that:

maps the first projection data of the first projection onto a virtual detector, maps the second projection data of the second projection onto the virtual detector, filters the first mapping data in such a way as to generate mapping data that originates from both the first projection data and the second projection data, filters the second projection data in such a way as to generate mapping data that originates from both the first projection data and the second projection data, generates a modified first projection by a reversal of the filtered first mapping data, generates a modified second projection by a reversal of the filtered second mapping data, and generates a 3D reconstruction image using a filtered back projection procedure based on the modified first projection and the modified second projection independently.

* * * * *